(12) United States Patent
Potula et al.

(10) Patent No.: US 8,742,150 B2
(45) Date of Patent: Jun. 3, 2014

(54) CASTOR OIL FATTY ACID BASED ESTOLIDE ESTERS AND THEIR DERIVATIVES AS POTENTIAL LUBRICANT BASE STOCKS

(75) Inventors: Satya Bhaskar Potula, Hyderabad (IN); Venkata Padmaja Korlipara, Hyderabad (IN); Venkata Surya Koppeswara Rao Bhamidipati, Hyderabad (IN); Saravanan Krishnasamy, Hyderabad (IN); Badari Narayana Prasad Rachapudi, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 680 days.

(21) Appl. No.: 12/992,546

(22) PCT Filed: May 14, 2009

(86) PCT No.: PCT/IN2009/000283
§ 371 (c)(1),
(2), (4) Date: May 31, 2011

(87) PCT Pub. No.: WO2009/139003
PCT Pub. Date: Nov. 19, 2009

(65) Prior Publication Data
US 2011/0282084 A1 Nov. 17, 2011

(30) Foreign Application Priority Data

May 14, 2008 (IN) .......................... 1202/DEL/2008

(51) Int. Cl.
*C07C 59/00* (2006.01)
*C07C 69/34* (2006.01)

(52) U.S. Cl.
USPC ........... 554/219; 554/213; 554/121; 508/463; 508/465

(58) Field of Classification Search
None
See application file for complete search history.

(56) References Cited

U.S. PATENT DOCUMENTS 2,156,737 A * 5/1939 Priester .......................... 554/122
2,785,978 A * 3/1957 De Rijck ....................... 426/611
4,652,406 A * 3/1987 Lepper et al. ................. 554/167
6,018,063 A    1/2000 Isbell et al.
6,316,649 B1  11/2001 Cermak et al.
6,407,272 B1   6/2002 Nelson et al.

FOREIGN PATENT DOCUMENTS

GB           590386       *  7/1947

OTHER PUBLICATIONS

Hawke, F., et al., The Auto-Reactions of ricinoleic cid Part I. Reactins at 180C, 147C, 122.3C and room temperature, 1959, Journal of the South African Chemical Institute, vol. XII, pp. 1-16.*
Harry-O'Kuru, R.E., et al., Synthesis of estolide esters from cis-9-octadecenoic acid estolides, 2001, JAOCS, vol. 78, No. 3, pp. 219-222.*
Patwari, A.A., et al., Kinetics of reactoin for preparation of ricinoleic acid from castot oil, 2000, Journal of the Oil Technologists' Association of India, vol. 32, No. 3, pp. 115-119.*
Yoshida, Y. et al., Enzymatic synthesis of estolides by a bioreactor, 1997, JAOCS, vol. 74, No. 3, pp. 261-267.*
Teeter, H.M., et al., Synthetic lubricants from hydroxystearic acids, 1953, Ind. Eng. Chem. vol. 45, No. 8, pp. 1777-1779.*
Isbell, et al., "Physical Properties of Triglyceride Estolides from Lesquerella and Castor Oils," Industrial Crops and Products, May 2006, pp. 256-263, vol. 23, No. 3, Elsevier, Maryland Heights, MO, USA.
Modak, et al., "Studies in Estolides. I. Kinetics of Estolide Formation and Decomposition," Journal of the American Oil Chemists' Society, 1965, pp. 428-432, vol. 42, Springer, New York, NY, USA.
Phillips, et al., "Glycerides of Monnina Emarginata Seed Oil," Biochimica et Biophysica Acta, Oct. 1970, pp. 71-82, vol. 218, No. 1, Elsevier, Maryland Heights, MO, USA.
Venkatesan, "Studies in Estolides, Part III: Plasticizer for Polyvinyl Chloride," Journal of the American Oil Chemists' Society, 1978, pp. 569-570, vol. 56, Springer, New York, NY, USA.

* cited by examiner

Primary Examiner — Yate K Cutliff
(74) Attorney, Agent, or Firm — Blank Rome LLP

(57) ABSTRACT

Castor oil was hydrolysed to castor fatty acids and self condensed to get a ricinoleic acid-based estolide of about 95 acid value. The carboxylic group of the estolide on subsequent esterification with linear or branched chain alcohols and also on acetylation of free hydroxy group yielded castor oil fatty acids based estolide esters and their acetates. All the products were evaluated for total acid number (TAN), viscosity, viscosity index, pour point, flash point, and copper strip corrosion and found to be potential lubricant basestocks.

7 Claims, No Drawings

CASTOR OIL FATTY ACID BASED ESTOLIDE ESTERS AND THEIR DERIVATIVES AS POTENTIAL LUBRICANT BASE STOCKS

FIELD OF THE INVENTION

This invention relates to preparation of straight chain and isoalkyl esters of castor oil fatty acid-based estolides and their derivatives as potential lubricant base stocks.

BACKGROUND OF THE INVENTION

Vegetable oils are considered to be potential candidates for the preparation of biolubricant base stocks to replace conventional mineral oil-based lubricating oils and synthetic esters. Vegetable oil based lubricants are attractive alternatives to mineral oil-based lubricants due to their enhanced biodegradability, lower toxicity and several other properties.

Estolides are a class of esters, based on vegetable oils that form when the carboxylic acid functionality of one fatty acid reacts at the site of unsaturation or double bond, of another fatty acid to form an ester linkage, and the product is popularly known as estolides. The secondary linkages of the estolides are more resistant to hydrolysis than triglycerides, and the unique structure of the estolide results in materials that have physical properties far superior to those of vegetable and mineral oils for certain applications [Inform, 15, p. 515 (2004)].

Esters of estolides derived from oleic acids and $C_6$ to $C_{14}$ saturated fatty acids, characterized by superior properties for use as lubricant base stocks have been described in Industrial Crops and Products (2001), 13(1), 11-20. In another study saturate-capped, oleic estolides were esterified with 2-ethylhexanol to obtain the corresponding ester [Industrial Crops and Products, 18, p. 183 (2003); U.S. Pat. No. 6,018,063 (2002) & U.S. Pat. No. 6,316,649 (2001)]. These coco-oleic estolide esters displayed superior low temperature properties (−36° C.) and more suitable as a base stock for biodegradable lubricants and functional fluids than current vegetable oil-based commercial materials.

In the another type of estolides, hydroxy fatty acids of castor oil can be readily converted into estolides by homopolymerization [J. Am. Oil Chem. Soc. 42; p. 428 (1965). Unlike normal estolides, that are formed when the carboxylic acid functionality of one fatty acid links to the site of unsaturation of another fatty acid to form oligomeric esters, the fatty acids of castor have a hydroxy functionality that provides a site for esterification to take place to produce estolides.

Castor oil is an attractive industrial raw material for the preparation of several functional compounds including lubricants [J. Am. Oil Chem. Soc. 51, p. 65 (1974), J. Am. Oil Chem. Soc. 48, p. 758 (1971)]. The presence of ricinoleic acid (hydroxyl fatty acid (12-hydroxy 9 cis-octadecenoic acid)) up to 85-90% projects castor oil as an attractive lubricant base stock.

Secondary alcohol esters of hydroxy acids, e.g., ricinoleate esters of secondary alcohols, are prepared by reacting an ester of a hydroxy acid with a secondary alcohol, in the presence of a organo metallic transesterification catalyst have been reported in U.S. Pat. No. 6,407,272 (2002), which are useful as a lubricity agent.

Estolides of lesquerella and castor triglycerides with oleic acid have been reported in Journal of the American Oil Chemists' Society, 79, p. 1227 (2002). Synthesis and physical properties of lesquerella and castor hydroxy triglycerides was reported in Industrial Crops and Products, 23, p. 256 (2006). Lesquerella and castor oils were converted to their corresponding estolides by reacting with saturated fatty acids ($C_2$-$C_{18}$) in the presence of a tin 2-ethylhexanoate catalyst (0.1 wt. %) and utilizing the condensation of hydroxy with corresponding anhydride or heating under vacuum at 200° C.

Estolides of lesquerella and castor fatty acids with different types of saturated, unsaturated and branched fatty acids have been reported in Industrial Corps and Products, 23, p 54 (2006). Castor and lesquerella estolide esters had the best cold temperature properties when capped with oleic or a branched fatty acid. As the saturation in the estolide increased pour and cloud points also increased

OBJECTIVES OF THE INVENTION

The main objective of the present invention is to prepare castor oil fatty acid-based estolides and their acetate.

Another objective of the invention is to prepare linear and isoalkyl esters of the above estolides A further objective of the invention is to convert the alkyl and isoalkyl esters of the estolides to their acetates to reduce the viscosity without substantially affecting the pour point and flash points.

Yet another objective of the invention is to established the formation of both ester and acetate moieties in the crude estolides by $^1$H NMR studies.

It is also an objective of the invention to provide the physico-chemical properties of these esters.

It is a further objective of this invention to provide a family of estolides which are biodegradable and which have required oxidative stability, low temperature and viscometric properties Other objectives and advantages of this invention will become readily apparent from the ensuing description.

SUMMARY OF THE INVENTION

In the present invention a family of a novel estolide compounds derived from castor oil fatty acids estolides with about an acid value of 95 is reported. The castor oil fatty acids used in this invention contains not less than 84% of ricinoleic acid.

DETAILED DESCRIPTION OF THE INVENTION

Accordingly, the present invention provides an estolide compound of general formula 1

General Formula 1

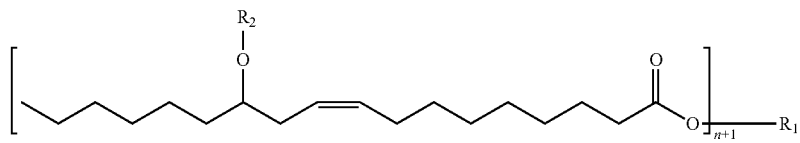

Wherein value of n is 1, wherein average value of n equal, one having acid value of estolide equal to 95 which correspond to average of two molecules of ricinoleic acid in the estolide R1 is hydrocarbon branched or unbranched of C1 to C8; $R_2$ moiety is selected from a group consisting of hydrogen, $CH_3CO$.

In an embodiment of the invention wherein $R_1$ moiety is selected from a group consisting of methyl, iso-propyl, butyl, hexyl, 2-ethylhexyl, and $R_2$ moiety is selected from a group consisting of hydrogen, $CH_3CO$.

Accordingly the present invention also provides a process for preparation of estolide of general formula 1 as claimed in claim 1 wherein the process comprising;
(i) saponifying castor oil to obtain the ricinoleic acid, heating the ricinoleic acid at temperature ranging between 175 to 190° C. under inert atmosphere for a period ranging between 3 to 5 hr to obtain estolide compound of formula 1 wherein the average value of n is 1 and, $R_1$ & $R_2$ are H,
(ii) reacting the estolide compound 1 obtained in step (i) with an alcohol of carbon C1-C8 such as methanol, isopropanol, butanol, n-hexanol, 2-ethylhexanol, in presence of a catalyst selected from sulphuric acid or $SnCl_2$ at reflux temperature or a temperature ranging between 140 to 160° C. for a period ranging between 3 to 8 hr to obtain corresponding estolide ester,
(iii) reacting the estolide ester obtained in step (ii) with acetic anhydride and pyridine to obtain the acetyl compound of estolide ester of general formula 1 wherein $R_1$ moiety is selected from a group consisting of methyl, iso-propyl, butyl, hexyl, 2-ethylhexyl, and $R_2$ moiety is $CH_3CO$.

In an embodiment of the invention wherein the acid number of the compounds is 0.5 mg KOH/g In another embodiment of the invention wherein the compounds of formula 1 are suitable as base stock of functional fluids as such and with blends and additives.

The vegetable oil based lubricants of the invention are prepared from triglycerides composed of fatty acids with one hydroxyl group and one site of unsaturation as major constituent in addition to non hydroxy saturated and unsaturated fatty acids and most preferred source is castor oil.

Castor oil contains about 85-90% of ricinoleic acid (12-hydroxy-9-cis-octadecenoic acid) is converted to its fatty acids by saponification route. The resultant castor oil fatty acids (AV 195) are homopolymerized to ricinoleic acid-based estolides of about 95 acid value at elevated temperatures under reduced pressure. During this step Acid value was reduced from 195 to 95 indicating the formation of estolide.

In the next step the estolides are converted to linear and isoalkyl esters in presence of a catalyst using linear and isoalkyl alcohols. Finally these esters are acetylated by using an acetylating agent consisting of a mixture of acetic anhydride and pyridine.

Products formed were of following structures where $R_1$ is an alkyl chain and $R_2$ is H or acetyl group.

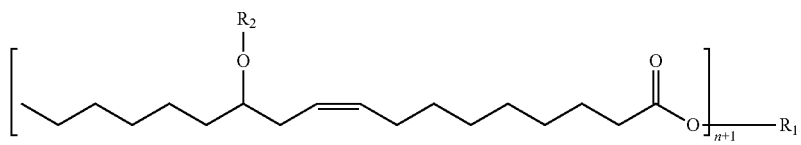

Where average value of n=1 (corresponding to acid value of 95)

The formation of both ester and acetate moieties in the products were established by $^1H$ NMR spectral studies. $^1H$ NMR spectra of all the products clearly established the formation of alkyl ester and acetate groups in the respective crude estolides.

All the products were evaluated for total acid number (TAN), viscosity, viscosity index, pour point, flash point, and copper strip corrosion and found to be potential lubricant basestocks.

The advantages of the present invention are that these products are synthesized from renewable resource like castor oil which is non-edible. The products synthesized exhibited high viscosity index, high flash point and low pour point characteristics.

This invention is further described by the following examples which are given only for the purpose of illustration and not indented to limit the scope of the invention. Although the invention has been described in conjunction with examples and by reference to the embodiments thereof, it is evident that many alternative modifications and variations will be apparent to those skilled in the art in light of the forging description, accordingly it is intended in the invention to embrace these and all such alternatives, variations and modifications as may fall with in the spirit and scope of the appended claims.

Example 1

Preparation of Estolides of Castor Oil Fatty Acids

Castor oil (1000 g) was taken in a three necked round bottom flask and heated to 80° C. A solution of sodium hydroxide (145 g, sodium hydroxide/1200 ml, water) was slowly added to it under stirring. Stirring was continued for 3 hours at 85° C. On completion of saponification a sufficient amount of dilute aqueous hydrochloric acid solution (6 N) was added to the reaction mixture to completely decompose fatty acid soap at pH which is less than 4. Stirring was continued for 15 minutes. The reaction mixture was cooled to room temperature and extracted with ether. Ether layer was washed with water to remove hydrochloric acid. The organic layer was passed through sodium sulphate to remove suspended water. Ether was removed under vacuum to get castor oil fatty acids with yield of 920 g. Ricinoleic acid (800 g) was heated to 185° C. with stirring under nitrogen. Periodically sample was withdrawn to monitor the acid value to determine the extent of estolide formation. Reaction was terminated on achieving the desired acid value of 95, the theoretical acid value of estolide with two units of ricinoleic acid. The yield of the product was 720 g.

Example 2

Preparation of Estolide Methyl Ester

Castor oil fatty acid estolide (400 g) having acid value of 95 was refluxed with methanol (4000 ml) containing 2% sulphuric acid. The course of esterification was monitored by thin layer chromatography. On completion of the reaction the contents were cooled, extracted with ethyl acetate and washed with water. Organic layer was passed through sodium sulphate and excess alcohol and ethyl acetate was distilled under reduced pressure. The yield of the product was 401 g with the following properties.

| | |
|---|---|
| Acid number, mg KOH/g: | 0.26 |
| Viscosity at 40° C.: | 32.97 |
| Viscosity at 100° C.: | 6.20 |
| Viscosity Index: | 162 |
| Pour point (° C.): | −33 |
| Flash point (° C.): | 252 |
| Cu strip corrosion value: | 1a |

The crude product was subjected to $^1$H NMR spectral studies to establish the formation of estolide methyl ester.

$^1$H NMR (CDCl$_3$, ppm): 0.9 [m, 2x-CH$_3$], 1.2-1.6 [m, 22x-CH$_2$—], 2.0 [m, 2x-CH$_2$—CH═CH—], 2.1-2.4 [m, 2x-CO—CH$_2$—], 3.5-3.7 [m, —CH—OH, —O—CH$_3$], 4.8 [m, —O—CH—], 5.2-5.6 [m, 2x-C$\underline{H}$═C$\underline{H}$—CH$_2$—]

Example 3

Preparation of Acetate of Estolide Methyl Ester

Estolide methyl ester was acetylated by using an acetylating reagent consisting of a mixture of acetic anhydride (110 ml) and pyridine (330 ml). The acetylating agent was added to estolide methyl ester (220 g) and refluxed until acetylation reaction was completed. Subsequently reaction mixture was cooled to room temperature, extracted with ether and treated with sufficient quantity of dilute hydrochloric acid to neutralize the pyridine. Ether layer was washed with water to make it free from acid and passed through sodium sulfate. Ether was removed under reduced pressure. Drying under vacuum gave 197 g of acetylated product with the following properties

| | |
|---|---|
| Acid number, mg KOH/g: | 0.49 |
| Viscosity at 40° C.: | 17.38 |
| Viscosity at 100° C.: | 4.22 |
| Viscosity Index: | 164 |
| Pour point (° C.): | −33 |
| Flash point (° C.): | 252 |
| Cu strip corrosion value: | 1a |

The crude product was subjected to $^1$H NMR spectral studies to establish the formation of acetate of estolide methyl ester.

$^1$H NMR (CDCl$_3$, ppm): 0.9 [m, 2x-CH$_3$], 1.2-1.4 [m, 22x-CH$_2$], 1.9-2.0 [m, 2x-CH$_2$—CH═CH, —CO—CH$_3$] 2.2 [m, 2x-CO—CH$_2$—], 3.6 [s-O—CH$_3$], 4.8 [m, 2x-O—CH—], 5.2-5.4 [m, 2x-C$\underline{H}$═C$\underline{H}$—CH$_2$—]

Example 4

Preparation of Estolide Isopropyl Ester

Castor oil fatty acid estolide (571 g) were refluxed with isopropanol (118 ml) containing 2% sulphuric acid. The course of esterification was monitored by thin layer chromatography. On completion of the reaction the contents were cooled, extracted with ethyl acetate and washed with water. Organic layer was passed through sodium sulphate and excess alcohol and ethyl acetate was distilled under reduced pressure. The yield of the product was 594 g with the following properties

| | |
|---|---|
| Acid number, mg KOH/g: | 0.03 |
| Viscosity at 40° C.: | 39.90 |
| Viscosity at 100° C.: | 7.28 |
| Viscosity Index: | 149 |
| Pour point (° C.): | −27 |
| Flash point (° C.): | 252 |
| Cu strip corrosion value: | 1a |

The crude product was subjected to $^1$H NMR spectral studies to establish the formation of estolide isopropyl ester.

$^1$H NMR (CDCl$_3$, ppm): 0.9 [m, 4x-CH$_3$], 1.2-1.6 [m, 22x-CH$_2$—], 2.0 [m, 2x-CH$_2$—CH═CH—], 2.2-2.4 [m, 2x-CO—CH$_2$—], 3.6 [m, —CH—OH], 4.8-5.0 [m, 2x-O—CH—], 5.3-5.5 [m, 2x C$\underline{H}$═C$\underline{H}$—CH$_2$—]

Example 5

Preparation of Acetate of Estolide Isopropyl Ester

Estolide isopropyl ester was acetylated by using an acetylating reagent consisting of a mixture of acetic anhydride (100 ml) and pyridine (300 ml) in 1:3 v/v ratios. The acetylating agent was added to estolide isopropyl ester (220 g) and refluxed until acetylation reaction was completed. Subsequently reaction mixture was cooled to room temperature, extracted with ether and treated with sufficient quantity of dilute hydrochloric acid to neutralize the pyridine. Ether layer was washed with water to make it free from acid and passed through sodium sulfate. Ether was removed under reduced pressure. Drying under vacuum gave 214 g of acetylated product with the following properties.

| | |
|---|---|
| Acid number, mg KOH/g: | 0.08 |
| Viscosity at 40° C.: | 31.27 |
| Viscosity at 100° C.: | 6.73 |
| Viscosity Index: | 181 |
| Pour point (° C.): | −30 |
| Flash point (° C.): | 252 |
| Cu strip corrosion value: | 1a |

The crude product was subjected to $^1$H NMR spectral studies to establish the formation of acetate of estolide isopropyl ester $^1$H NMR (CDCl$_3$, ppm): 0.9 [m, 4x-CH$_3$], 1.2-1.6 [m, 22x-CH$_2$—], 2.0 [m, 2x-CH$_2$—CH═CH—, O—CO—CH$_3$] 2.2-2.5 [m, 2x-CO—CH$_2$—], 4.8-5.0 [m, 2x-O—CH—], 5.3-5.5 [m, 2x-C$\underline{H}$═C$\underline{H}$—CH$_2$—]

Example 6

Preparation of Estolide Butyl Ester

Castor oil fatty acid estolide (62.5 g) were refluxed with butanol (100 ml) containing 1% sulphuric acid. On completion of the reaction the contents were cooled, extracted with ethyl acetate and washed with water. Organic layer was passed through sodium sulphate and excess alcohol and ethyl acetate was distilled under reduced pressure. The yield of the product was 64.3 g with the following properties.

| | |
|---|---|
| Acid number, mg KOH/g: | 0.24 |
| Viscosity at 40° C.: | 70.39 |
| Viscosity at 100° C.: | 12.38 |
| Viscosity Index: | 176 |

The crude product was subjected to $^1$H NMR spectral studies to establish the formation of estolide butyl ester $^1$H NMR (CDCl$_3$, ppm): 0.9 [m, 3x-CH$_3$], 1.2-1.6 [m, 24x-CH$_2$—], 2.0 [m, 2x-CH$_2$—CH=CH—], 2.2-2.3 [m, 2x-CO—CH$_2$—], 3.5 [m, —CH—OH], 4.0 [t, —O—CH$_2$—], 4.8 [m, O—CH—], 5.3-5.4 [m, 2x-CH=CH—CH$_2$—]

Example 7

Preparation of Acetate of Estolide Butyl Ester

Estolide butyl ester was acetylated by using an acetylating reagent consisting of a mixture of acetic anhydride (100 ml) and pyridine (300 ml) in 1:3 v/v ratios. The acetylating agent was added to estolide butyl ester (220 g) and refluxed until acetylation reaction was completed. Subsequently reaction mixture was cooled to room temperature, extracted with ether and treated with sufficient quantity of dilute hydrochloric acid to neutralize the pyridine. Ether layer was washed with water to make it free from acid and passed through sodium sulfate. Ether was removed under reduced pressure. Drying under vacuum gave 204 g of acetylated product with the following properties.

| | |
|---|---|
| Acid number, mg KOH/g: | 0.1 |
| Viscosity at 40° C.: | 25.40 |
| Viscosity at 100° C.: | 6.30 |
| Viscosity Index: | 216 |
| Cu strip corrosion value | 1a |

The crude product was subjected to $^1$H NMR spectral studies to establish the formation of acetate of estolide butyl ester.

$^1$H NMR (CDCl$_3$, ppm): 0.9 [m, 3x-CH$_3$], 1.2-1.6 [m, 24x-CH$_2$], 2.0 [m, 2x-CH$_2$—CH=CH—, O—CO—CH$_3$], 2.2-2.3 [m, 2x-CO—CH$_2$—], 2.7 [m, —CH—OH], 4.0 [t, —O—CH$_2$—], 4.0 [m, 2x-O—CH—], 5.3-5.4 [m, 2x-CH=CH—CH$_2$—]

Example 8

Preparation of Estolide n-Hexyl Ester

Castor oil fatty acid estolide (66 g) were refluxed with n-hexanol (660 ml) containing 0.1% SnCl$_2$. On completion of the reaction the contents were cooled, extracted with ethyl acetate and washed with water. Organic layer was passed through sodium sulphate and excess alcohol and ethyl acetate was distilled under reduced pressure. The yield of the product was 69.2 g with the following properties

| | |
|---|---|
| Acid number, mg KOH/g: | 0.074 |
| Viscosity at 40° C.: | 56.3 |
| Viscosity at 100° C.: | 10.13 |
| Viscosity Index: | 169 |
| Pour point (° C.): | −24 |
| Flash point (° C.): | 252 |
| Cu strip corrosion value | 1a |

The crude product was subjected to $^1$H NMR spectral studies to establish the formation of estolide n-hexyl ester $^1$H NMR (CDCl$_3$, ppm): 0.9 [m, 3x-CH$_3$], 1.2-1.6 [m, 26x-CH$_2$], 2.0 [m, 2x-CH$_2$—CH=CH—], 2.2-2.4 [m, 2x-CO—CH$_2$—], 3.5 [m, CH—OH], 4.0 [t, O—CH$_2$—], 4.8 [m, —O—CH—], 5.2-5.5 [m, 2x-CH=CH—CH$_2$—]

Example 9

Preparation of Estolide 2-Ethylhexyl Ester

Castor oil fatty acid estolide (700 g) were refluxed with 2-ethylhexanol (374 ml) containing 0.1% SnCl$_2$. On completion of the reaction the contents were cooled, extracted with ethyl acetate and washed with water. Organic layer was passed through sodium sulphate and excess alcohol and ethyl acetate was distilled under reduced pressure. The yield of the product was 808 g with the following properties.

| | |
|---|---|
| Acid number, mg KOH/g: | 0.49 |
| Viscosity at 40° C.: | 63.79 |
| Viscosity at 100° C.: | 10.09 |
| Viscosity Index: | 144 |
| Pour point (° C.): | −36 |
| Flash point (° C.): | 252 |
| Cu strip corrosion value | 1a |

The crude product was subjected to $^1$H NMR spectral studies to establish the formation of estolide 2-ethylhexyl ester.

$^1$H NMR (CDCl$_3$, ppm): 0.9 [m, 4x-CH$_3$], 1.2-1.6 [m, 26x-CH$_2$], 2.0 [m, 2x-CH$_2$—CH=CH—], 2.2-2.3 [m, 2x-CO—CH$_2$—], 3.5 [m, —CH—OH], 4.0 [d, O—CH$_2$—], 4.8 [m, —O—CH—], 5.2-5.5 [m, 2x CH=CH—CH$_2$—]

Example 10

Preparation of Acetate of Estolide 2-Ethylhexyl Ester

Estolide 2-ethylhexyl ester was acetylated by using an acetylating reagent consisting of a mixture of acetic anhydride (153 ml) and pyridine (459 ml). The acetylating agent was added to estolide 2-ethylhexyl (373 g) and refluxed until acetylation reaction was completed. Subsequently reaction mixture was cooled to room temperature, extracted with ether and treated with sufficient quantity of dilute hydrochloric acid to neutralize the pyridine. Ether layer was washed with water to make it free from acid and passed through sodium sulfate. Ether was removed under reduced pressure. Drying under vacuum gave 348 g of acetylated product with the following properties.

| | |
|---|---|
| Acid number, mg KOH/g: | 0.20 |
| Viscosity at 40° C.: | 42.7 |
| Viscosity at 100° C.: | 8.35 |
| Viscosity Index: | 175 |
| Pour point (° C.): | −39 |
| Flash point (° C.): | 262 |
| Cu strip corrosion value | 1a |

The crude product was subjected to $^1$H NMR spectral studies to establish the formation of acetate of estolide 2-ethylhexyl ester.

$^1$H NMR (CDCl$_3$, ppm): 0.9 [m, 4x-CH$_3$], 1.2-1.6 [m, 26x-CH$_2$—], 1.9-2.0 [m, 2x-CH$_2$—CH=CH—, O—CO—CH$_3$], 2.2-2.3 [m, 2x-CO—CH$_2$—], 3.9-4.0 [d, O—CH$_2$—], 4.8 [m, —O—CH—], 5.2-5.4 [m, 2x-CH=CH—CH$_2$—]

ADVANTAGES OF THE INVENTION

1. Advantages of the estolide derivatives of invention are their high viscosity index (VI) and viscosity grade of ISO VG 32 and above which are more desirable.
2. These estolide derivatives may not need thickeners which are necessary for improving the viscosity, VI and presence of polymer based thickeners or modifiers can cause shear stability problems in formulated lubricants.
3. Low temperature properties are important for lubricant pumpability, filterability, fluidity, as well as cold cranking and startups. Pour point is the most common indicator of the low temperature behavior. Base stocks derived from vegetable oils usually have high pour points without the addition of pour point depressants. The estolide derivatives of the invention have superior low temperature properties than trioleate, vegetable oils or polyol esters of higher viscosities.
4. In general the estolide derivatives of the invention are expected to have advantage over other vegetable oil based lubricants in their oxidative stability and low temperature properties.

We claim:

1. An estolide compound of general formula 1

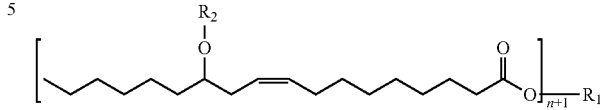

General Formula 1 wherein average value of n is equal to one having acid value of estolide equal to 95 which correspond to average of two molecules of ricinoleic acid in the estolide; R1 is branched or unbranched hydrocarbon of C1 to C8; and $R_2$ is $CH_3CO$.

2. An estolide compound as claimed in claim 1, wherein $R_1$ is selected from a group consisting of methyl, iso-propyl, butyl, hexyl, and 2-ethylhexyl.

3. A process for preparation of the estolide compound of claim 1, wherein the process comprises
   (i) saponifying castor oil to obtain the ricinoleic acid;
   (ii) heating the ricinoleic acid at temperature ranging between 175 to 190° C. under inert atmosphere for a period ranging between 3 to 5 hr to obtain an estolide compound of

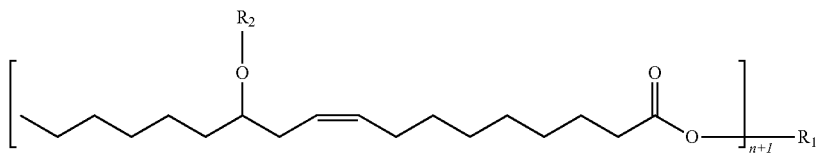

wherein the average value of n is 1 and, R1 and R2 are H;
   (iii) reacting the estolide compound obtained in step (ii) with an alcohol of carbon C1-C8 in presence of a catalyst selected from sulphuric acid or $SnCl_2$, at reflux temperature or a temperature ranging between 140 to 160° C. for a period ranging between 3 to 8 hr to obtain a corresponding estolide ester;
   (iv) reacting the estolide ester obtained in step (iii) with acetic anhydride and pyridine to obtain the compound of general formula 1 wherein R1 is branched or unbranched hydrocarbon of C1 to C8; and R2 is $CH_3CO$.

4. A process as claimed in claim 3, wherein the acid number of the compounds is 0.5 mg KOH/g.

5. A process as claimed in claim 3, wherein the compounds of formula 1 are suitable as base stock of functional fluids as such and with blends and additives.

6. A process as claimed in claim 3, wherein the alcohol of carbon C1-C8 is methanol, isopropanol, butanol, n-hexanol, or 2-ethylhexanol.

7. A process as claimed in claim 3, wherein $R_1$ of formula 1 in step (iv) is selected from a group consisting of methyl, iso-propyl, butyl, hexyl, and 2-ethylhexyl.

* * * * *